(12) United States Patent
Folch et al.

(10) Patent No.: US 7,501,279 B2
(45) Date of Patent: Mar. 10, 2009

(54) MICROWELL ARRAYS WITH NANOHOLES

(75) Inventors: Albert Folch, Seattle, WA (US); Turgut Fettah Kosar, Seattle, WA (US)

(73) Assignee: University of Washington, Seattle, WA (US)

(*) Notice: Subject to any disclaimer, the term of this patent is extended or adjusted under 35 U.S.C. 154(b) by 743 days.

(21) Appl. No.: 10/818,743

(22) Filed: Apr. 5, 2004

(65) Prior Publication Data

US 2006/0240543 A1    Oct. 26, 2006

Related U.S. Application Data

(60) Provisional application No. 60/460,249, filed on Apr. 3, 2003.

(51) Int. Cl.
*C12M 1/12* (2006.01)
(52) U.S. Cl. .................................. 435/297.5
(58) Field of Classification Search .............. 435/297.5
See application file for complete search history.

(56) References Cited

U.S. PATENT DOCUMENTS

| | | | |
|---|---|---|---|
| 4,894,343 A | 1/1990 | Tanaka et al. | 435/301 |
| 5,188,733 A | 2/1993 | Wang et al. | 210/321.84 |
| 5,605,662 A | 2/1997 | Heller et al. | 422/68.1 |
| 5,843,767 A * | 12/1998 | Beattie | 435/287.1 |
| 6,165,911 A * | 12/2000 | Calveley | 438/754 |
| 6,315,940 B1* | 11/2001 | Nisch et al. | 435/287.1 |
| 6,355,420 B1* | 3/2002 | Chan | 435/6 |
| 6,383,813 B1* | 5/2002 | Baxter et al. | 435/455 |
| 6,565,727 B1 | 5/2003 | Shenderov | 204/600 |
| 2003/0107386 A1* | 6/2003 | Dodgson et al. | 324/699 |
| 2006/0163063 A1* | 7/2006 | Picollet-Dahan et al. | 204/403.06 |

OTHER PUBLICATIONS

U.S. Appl. No. 60/153,677.*
PCT International Search Report dated Aug. 20, 2004 for International Application No. PCT/US04/10373.

* cited by examiner

*Primary Examiner*—Walter D Griffin
*Assistant Examiner*—Lydia Edwards
(74) *Attorney, Agent, or Firm*—Stoel Rives LLP

(57) ABSTRACT

A device for conducting parallel analysis or manipulation of multiple cells or biomolecules is disclosed. In one embodiment, the device comprises a silicon chip with a microwell, and at least one membrane suspended at the bottom opening of the microwell. The suspended portion of the membrane defines a nanohole that provides access to the material on the other side of the membrane.

21 Claims, 14 Drawing Sheets

MICROWELL ARRAYS WITH NANOHOLES

RELATED APPLICATIONS

This utility patent application claims the benefit of Provisional Application Ser. No. 60/460,249, filed Apr. 3, 2003. Provisional Application Ser. No. 60/460,249 is incorporated herein by reference.

FEDERALLY SPONSORED RESEARCH OR DEVELOPMENT

This invention was developed under NIH/NCRR Grant # 5 R21 RR16302, "Nanofluidic Probes for Recording/Stimulating Cell Behavior," Whitaker Foundation Grant # RG-00-0356, "Microarrays of Cellular Membrane Patches for High-Throughput Studies of Ion Channel Function," NASA Grant # NAG 9-1343, "Microarrays of Cellular Membrane Patches for In-Flight Studies of Ion Channel Function," and University of Washington, Center for Nanotechnology UIF Fellowship Award.

TECHNICAL FIELD

A device for conducting parallel analysis or manipulation of multiple cells or biomolecules is disclosed. The device may be used for a number of applications such as parallel patch-clamping, precision delivery of biochemical factors to cells, high-throughput screening for drug discovery, immunoisolation of cells, cellular and biomolecular separation, and protein and DNA sequencing.

BACKGROUND OF THE INVENTION

One of the biggest challenges in cell biology, as well as in neuroscience, is being able to do parallel analysis on multiple individual cells. This stems from the fact that most of the current cellular analysis tools and methods are not chemically sensitive enough for or physically capable of obtaining measurements from single cells. They also are not suitable (e.g. too bulky) to be implemented into automated systems for parallel analysis and require relatively extensive human labor. Furthermore, cell-based assays are becoming an essential step in high-throughput screening (HTS)-based drug discovery processes, increasing the demand for ever faster cell analysis tools. One solution of this problem is miniaturization of the cell analysis tools and methods using the state-of-the-art micro- and nanofabrication techniques. The device presented here is cheaper and more scalable than the conventional devices and has much higher throughput. It can be automated and do parallel analysis on multiple cells simultaneously. In addition, it requires much less expertise and operator time. Because of its flexible design, it can be used for a diverse range of applications such as parallel patch-clamping, precision delivery of biochemical factors to cells, high-throughput screening for drug discovery, immunoisolation of cells, cellular and biomolecular separation, and protein and DNA sequencing.

SUMMARY OF THE INVENTION

The lab-on-a-chip device described here is a new generation cell culture tool that allows the interrogation of large number of single cells simultaneously. The device enables parallel electrophysiological measurements, such as measuring ion currents through ion channels residing in the plasma membrane, as well as delivery of key biochemical factors to multiple cells with a very high precision. To achieve this, an array of very small holes is created on a thin transparent membrane of silicon nitride or silicon oxide that is suspended on an array of wells through a silicon wafer. A microfluidic channel network, made of poly(dimethylsiloxane) or another appropriate polymer, on the membrane side of the wafer allows individual addressing of the holes. Because the holes provide the sole fluidic and electrical connection between the microfluidic network on one side and the wells on the other side, very low-noise electrical measurements and well-controlled high-resolution delivery of biomolecules to cells can be achieved. Individual cells are cultured inside each well on top of or a certain distance away from the hole, depending on the application. The cells can also be cultured on the membrane side of the device, and the fluidic delivery can be done from the well-side. In addition, both sides of the device can be separately addressed via microfluidic channels. The device is useful for a number of other applications, such as high-throughput screening for drug discovery, immunoisolation of cells, cell filtration and separation, biomolecular separation, and protein and DNA sequencing.

Additional aspects and advantages of this invention will be apparent from the following detailed description of preferred embodiments, which proceeds with reference to the accompanying drawings.

BRIEF DESCRIPTION OF THE DRAWINGS

FIGS. 7-15 are perspective views, cross-sectional views and images of an embodiment of the device at different stages of fabrication.

DETAILED DESCRIPTION OF PREFERRED EMBODIMENTS

In one embodiment, the device is a lab-on-a-chip and is capable of automated, parallel, patch-clamp analysis of the effect of drug compounds on ion channels. The device can perform a high number of simultaneous patch-clamp evaluations with low drug compound and reagent consumption. For example, the device may have over 600 patch clamp units. The device is capable of performing independent modulation of chemical and electrical environment in each patch clamp unit. In the device, cells are automatically guided to the holes on the patch-clamp units by the application of suction from the opposite side of the hole. Each patch clamp unit may be individually addressed and is fluidically and electrically isolated from the rest of the units on the chip. The user can alter the electrical and chemical conditions of the solutions on either side of the cell. The device is further capable of rapid fluid exchange, which allows the study of ligand-gated ion channels.

Figure 1:
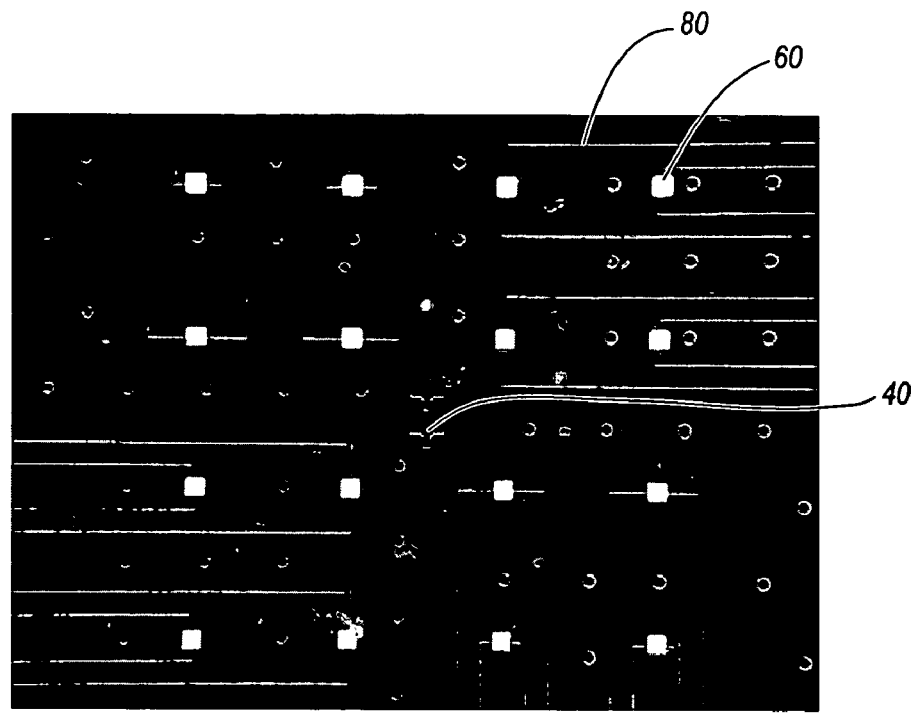
FIG. 1 is a microscope image of device comprising a 4-by-4 array of microwells and microchannels.

FIG. 1 is an image showing the top view of an embodiment of the device. The device comprises sixteen patch clamp units, each unit comprising a microwell 60 and a microchannel 80. Also seen in FIG. 1 are alignment marks 40. Alignment marks 40 assist in the manufacture of the device, as discussed in more detail below.

Figure 2:
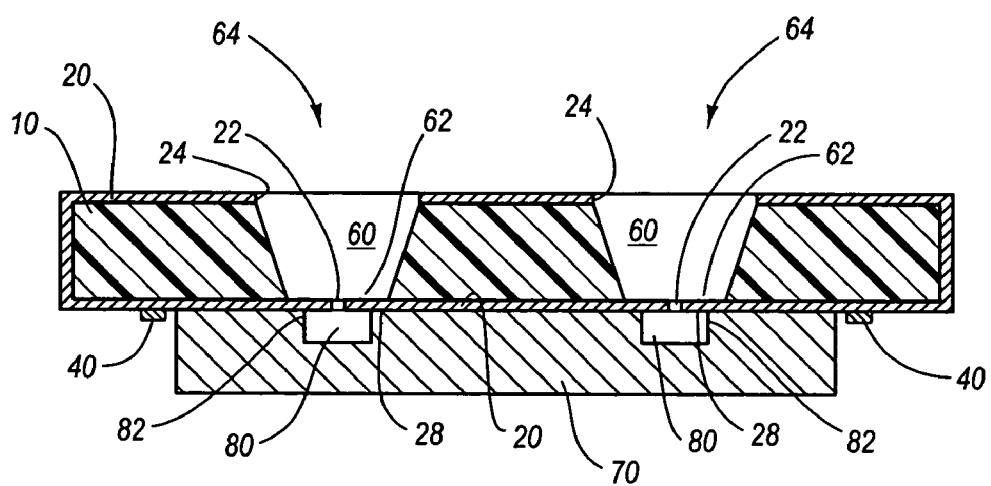
FIG. 2 is a cross-sectional view of one embodiment of the inventive device.

FIG. 2 is a cross-sectional view of an embodiment of the device adapted for patch clamping. The device comprises a substrate 10 that defines at least one microwell 60. Each microwell 60 comprises a top opening 64 so that the microwell can receive fluid. Each microwell further comprises a bottom opening 62. A silicon nitride membrane 20 surrounds substrate 10, except at top openings 64, where membrane 20 defines a window 24. At bottom opening 62 of each microwell 60, a portion 28 of membrane 20 is suspended and defines a nanohole 22. As a result, fluid placed in the microchannel is in fluid communication with the fluid in the microwell via the nanohole.

In the embodiment shown in FIG. 2, a microfluidic channel layer 70 comprises microchannels 80 with microchannel openings 82. Layer 70 is positioned below the substrate or wafer so that each microwell 60 and corresponding nanohole 22 is oriented over a microchannel opening 82. In the embodiment shown in FIG. 2, microchannels 80 are enclosed within channel layer 70 except at openings 82. In another embodiment (not shown) the microchannels may be exposed to the silicon nitride layer along their entire length.

In one embodiment, channel layer 70 comprises poly(dimethylsiloxane) ("PDMS"), a polymer that provides insulating properties for use in electrophysiological measurements. However, any polymer may be used that is capable of sealing to the silicon nitride layer, forming microchannels, and, for applications involving electricity, capable of providing insulation. For example, polyimide may be used for the channel layer.

Depending on the application and the desired results, a cell or biomolecule may be positioned on either side of the suspended membrane. For example, for patch clamping a cell may be placed on the microwell side of the suspended membrane.

The size of the nanohole can vary depending on the application. For example, for delivery of biomolecules to a cell, the nanoholes may range in size from about 1 to 100 microns. For patch-clamp experiments, nanoholes range in size from 0.5 micron to about 3 microns. For DNA or peptide sequencing, nanoholes range in size from about 1 to about 4 nanometers.

The embodiment shown in FIG. 2 is adapted for patch clamping on multiple individual cells. As shown in FIG. 2, each microchannel 80 has a portion 82 with an area below microwell bottom opening 62. Portion 82 is smaller than the area defined by the perimeter of microwell bottom opening 62. This configuration enables the microchannel to contain a fluid such that the fluid contacts only the suspended portion of the membrane. Stated otherwise, the configuration of the membrane, the microchannel and the microwell bottom opening prevents fluid contained in the microchannel from contacting a portion of the membrane that is below the substrate.

The following list provides some of the device's potential applications. The device may be used to do anything the conventional methods and devices do, but more accurately, more quickly, with less cost and less expertise. The first two of these applications are illustrated in FIGS. 3-6.

- Parallel electrophysiology on multiple individual cells (e.g. parallel patch-clamping)
- Precision delivery of biochemical factors to cells
- High-throughput screening (HTS) for drug discovery
- Immunoisolation of cells Cellular filtration and separation
Biomolecular separation
Protein and DNA sequencing Conventional patch-clamping is a common approach for evaluating the effect of compound on ion channels. Traditionally, patch-clamping involves sucking a portion of the cell membrane containing the ion channel of interest into the mouth of a pipette with about 1 micrometer internal diameter. A voltage is applied across the ion channel by placing electrodes in the electrolyte solution within the micropipette and the cell bath solution. Prospective drug compounds are then applied to the micropipette solution or the cell bath solution and the corresponding effects on ion channel function are evaluated.

Figure 3A:
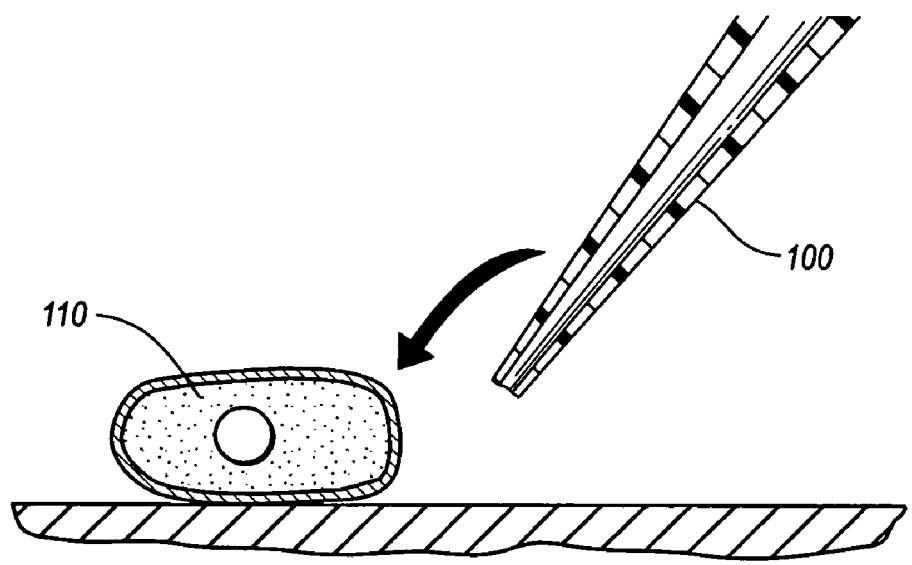
FIG. 3A is an illustration of traditional patch-clamping.
Figure 3B:
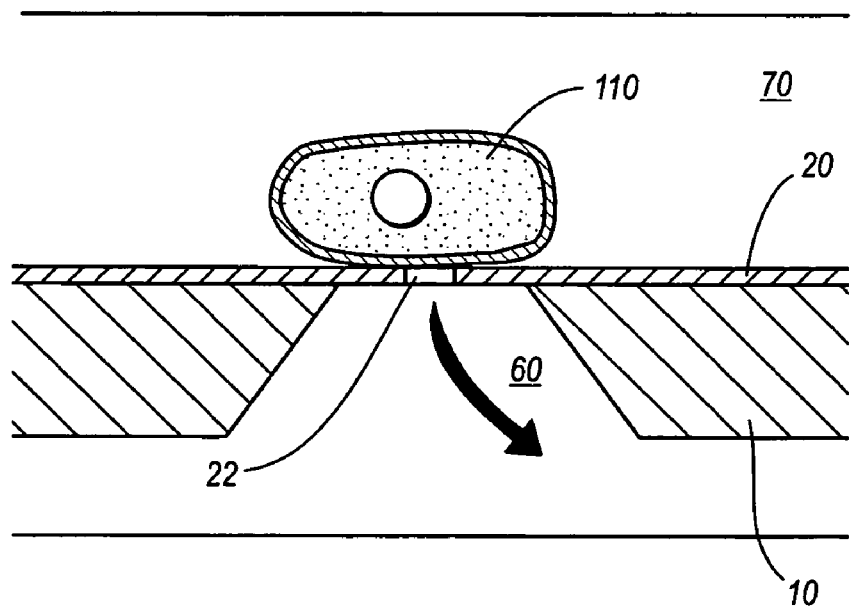
FIG. 3B is an illustration of patch-clamping using an embodiment of the inventive device.

FIG. 3A illustrates traditional patch clamping, which requires an operator to guide the tip of a micropipette 100 to a cell 110. FIG. 3B shows the operation of an embodiment of the inventive device. The device comprises a silicon wafer 10 having a silicon nitride membrane 20. FIG. 3B shows an expanded view of an embodiment of the invention designed for patch clamping. As shown in FIG. 3B, a nanohole 22 in membrane 20 is aligned with microwell 60. The device is capable of automatically guiding a cell 110 to nanohole 22 on the patch-clamp units when suction is applied to the opposite side of the nanohole.

Figure 4:
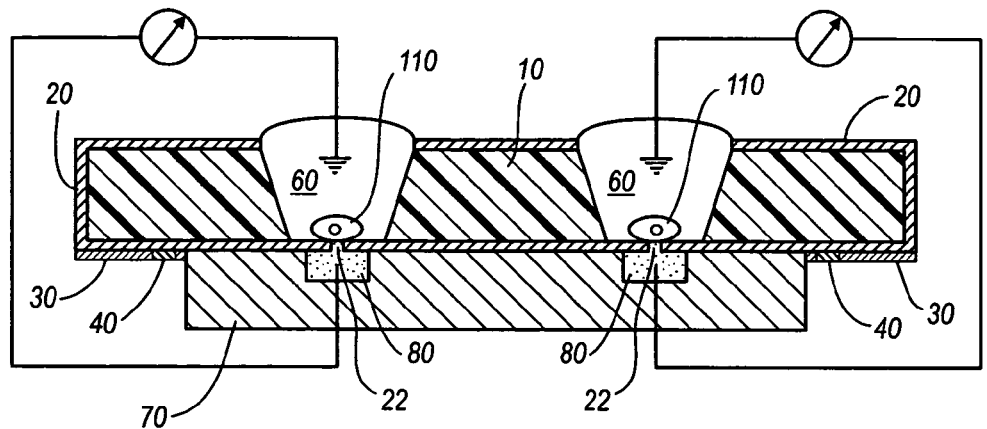
FIG. 4 is a cross-sectional view of one embodiment for in use for planar parallel patch-clamping.

FIG. 4 shows the use of the embodiment shown in FIGS. 1-2 for planar parallel patch-clamping. The electrical isolation of the silicon-backed sections of the silicon nitride membrane from the fluid (electrolyte) inside the microchannels enables the device to provide measurements with a minimal amount of noise. For example, meaningful measurements are generally taken in picoamperes ($10^{-12}$ amperes).

Figure 5:
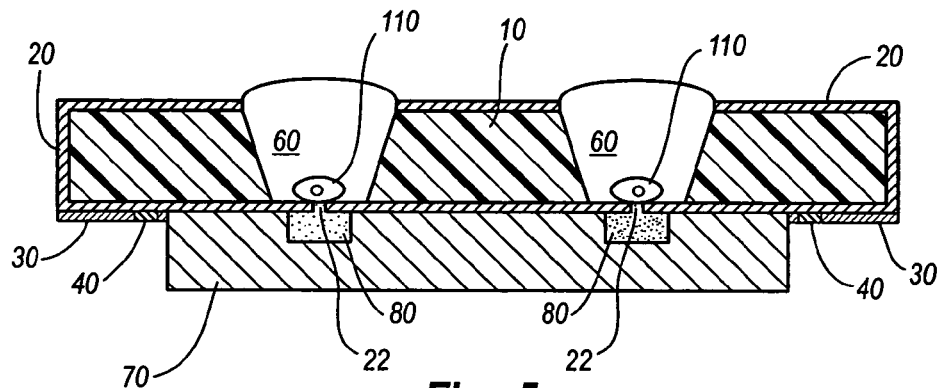
FIGS. 5-6 is a cross-sectional view of one embodiment of the device used for biomolecule nanodelivery to cells.
Figure 6:
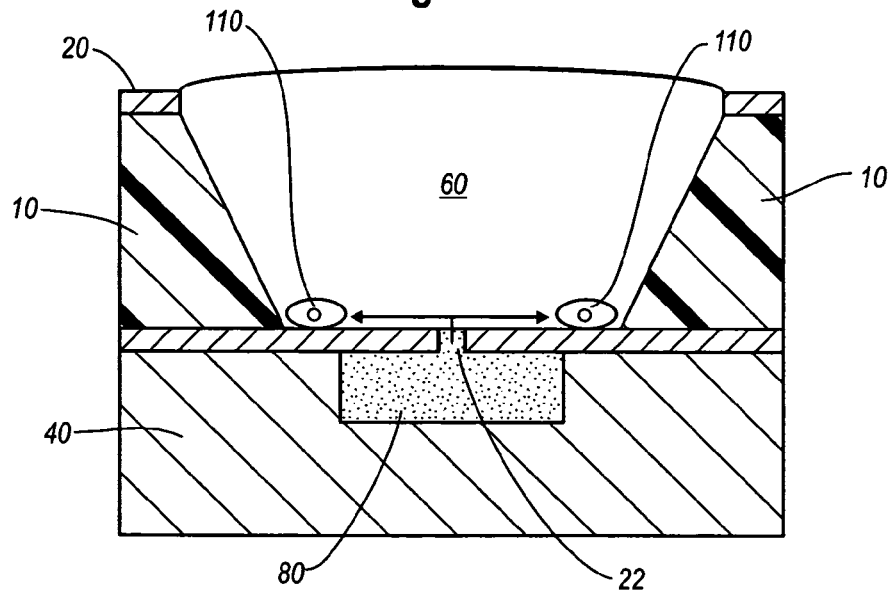

FIGS. 5-6 illustrate precision delivery of biochemical factors to cells. A different biomolecule solution may be delivered to each cell in the microwell 60 via the microchannels 80 and nanoholes 22. The device is adapted to achieve delivery of factors to a small area of the cell membrane. The device can deliver factors in a parallel fashion to multiple individual cells (i.e. high-throughput) and can be automated to save operational costs. In addition, use of the device for such delivery requires a relatively low level of skill and low levels of fluids and reagents.

The device may be used for efficient and reliable high-throughput screening for drug discovery. Screening may be conducted by patch clamping, as described above.

Other applications for the device include cellular filtration and separation. An embodiment for filtration comprises a suspended membrane defining multiple holes with precise diameters. The multiple holes are capable of action as filters. Some small cells may be allowed through the holes, while other, larger cells cannot pass through the holes. The separation can also be based on cell motility, where cells migrating on the surface of the suspended membrane or in the liquid medium travel to the other side through the holes. This application may be useful for separating healthy and motile spermatozoids from dead ones.

The device may be used for biomolecular separation. The holes on the membrane are fabricated small enough to permit proteins and biochemical factors up to a certain size to pass through the membrane. Separation can be driven by any suitable means, such as diffusion, pressure, electrical or magnetic fields and centrifugation.

The device may also be useful for protein and DNA sequencing. For this application, the nanoholes in the membrane may measure about 1 nanometer to about 4 nanometers, which is roughly the diameter range of single stranded DNA and proteins. To conduct sequencing, electrical current is passed through the device. As the molecules are forced through the hole, the electrical current that can flow through the hole changes in relation to size of each base or amino acid. The bases of DNA or amino acid of a peptide may then be determined from their characteristic current signatures.

The fabrication process of the device is described in connection with FIGS. 7-14.

Figure 7A:
FIG. 7A is a perspective view of a silicon wafer suitable for use in the device.
Figure 7B:
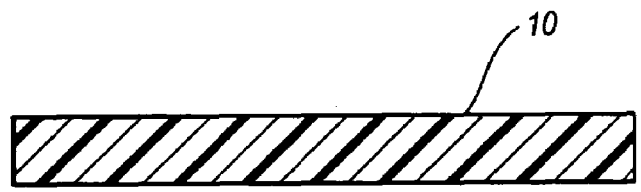
FIG. 7B is a cross-sectional view of a silicon wafer suitable for use in the device.

FIGS. 7A-7B show perspective and cross-sectional views of a standard or test grade silicon wafer 10 about 0.4 mm thick and with <100> crystal orientation. The wafer thickness may vary depending on the desired well size. Silicon, when etched, forms angled walls. As a result, the microwells have angled walls, as shown in FIG. 1. Because of this angle, a thinner wafer allows the microwells to be positioned closer together than a wafer of greater thickness.

Figure 8A:
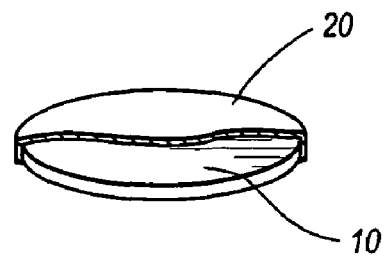
FIG. 8A is a perspective view of a silicon wafer with a silicon nitride membrane.
Figure 8B:
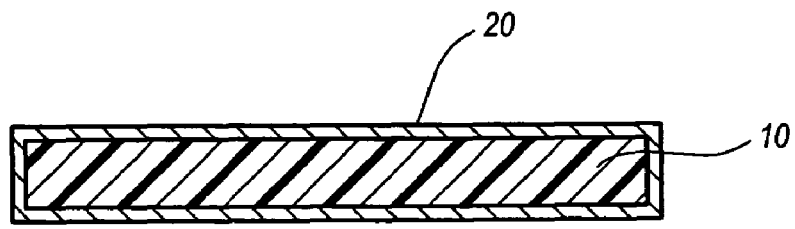
FIG. 8B is a cross-sectional view of a silicon wafer with a silicon nitride membrane.

A thin (200-2000 nm) layer 20 of low-stress silicon nitride is deposited on wafer 10, as shown in FIGS. 8A-8B. Layer 20 may be deposited by any conventional method, such as low pressure chemical vapor deposition ("LPCVD") or plasma enhanced chemical vapor deposition ("PECVD").

Figure 9A:
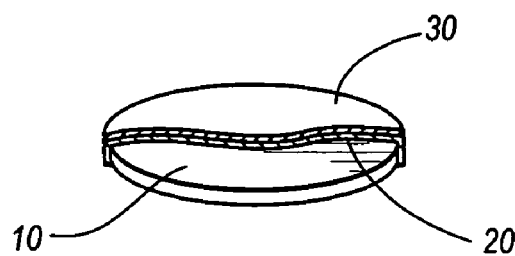
FIG. 9A is a perspective view of a silicon wafer with a layer of gold deposited above the silicon nitride on one side of the wafer.
Figure 9B:
FIG. 9B is a cross-section view of a silicon wafer with a layer of gold deposited above the silicon nitride on one side of the wafer.

After a layer of silicon nitride is deposited on the wafer, a layer of metal 30 is deposited on the top side of the wafer. Metal layer 30 is etched to create alignment marks used to orient the wafer, as discussed in more detail below. FIGS. 9A-9B illustrate this metal evaporation step. In a sputter or thermal evaporation system, a 100 nm layer 30 of gold (Au) is deposited on front side 12 of wafer 10 with a 10 nm layer of chromium (Cr) or titanium-tungsten alloy (TiW) (not shown) as the adhesion layer between silicon nitride and gold layers. Alternatively, layer 30 could be any metal that can be patterned by etching or dissolution. For example, a layer of chromium or titanium-tungsten alloy could be used instead of the gold layer.

Figure 10A:
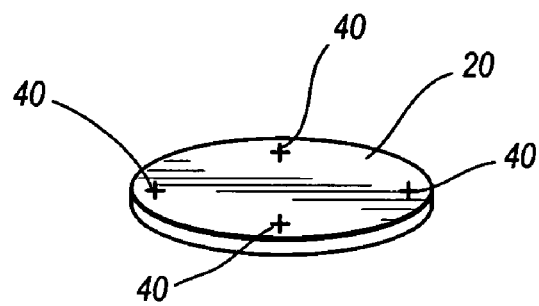
FIG. 10A is a perspective view of the wafer shown in FIGS. 9A-9B with alignment marks formed in the gold layer.
Figure 10B:
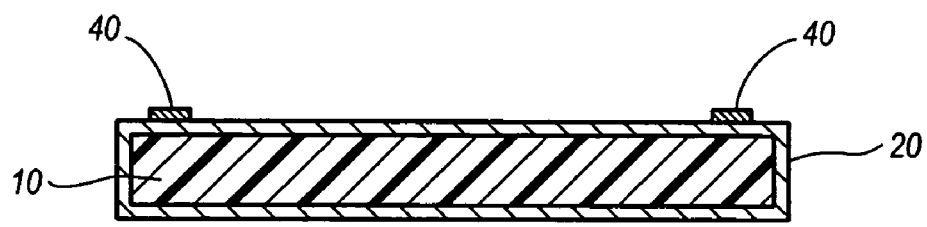
FIG. 10B is a cross-sectional view of the wafer shown in FIGS. 9A-B with alignment marks formed in the gold layer.
Figure 10C:
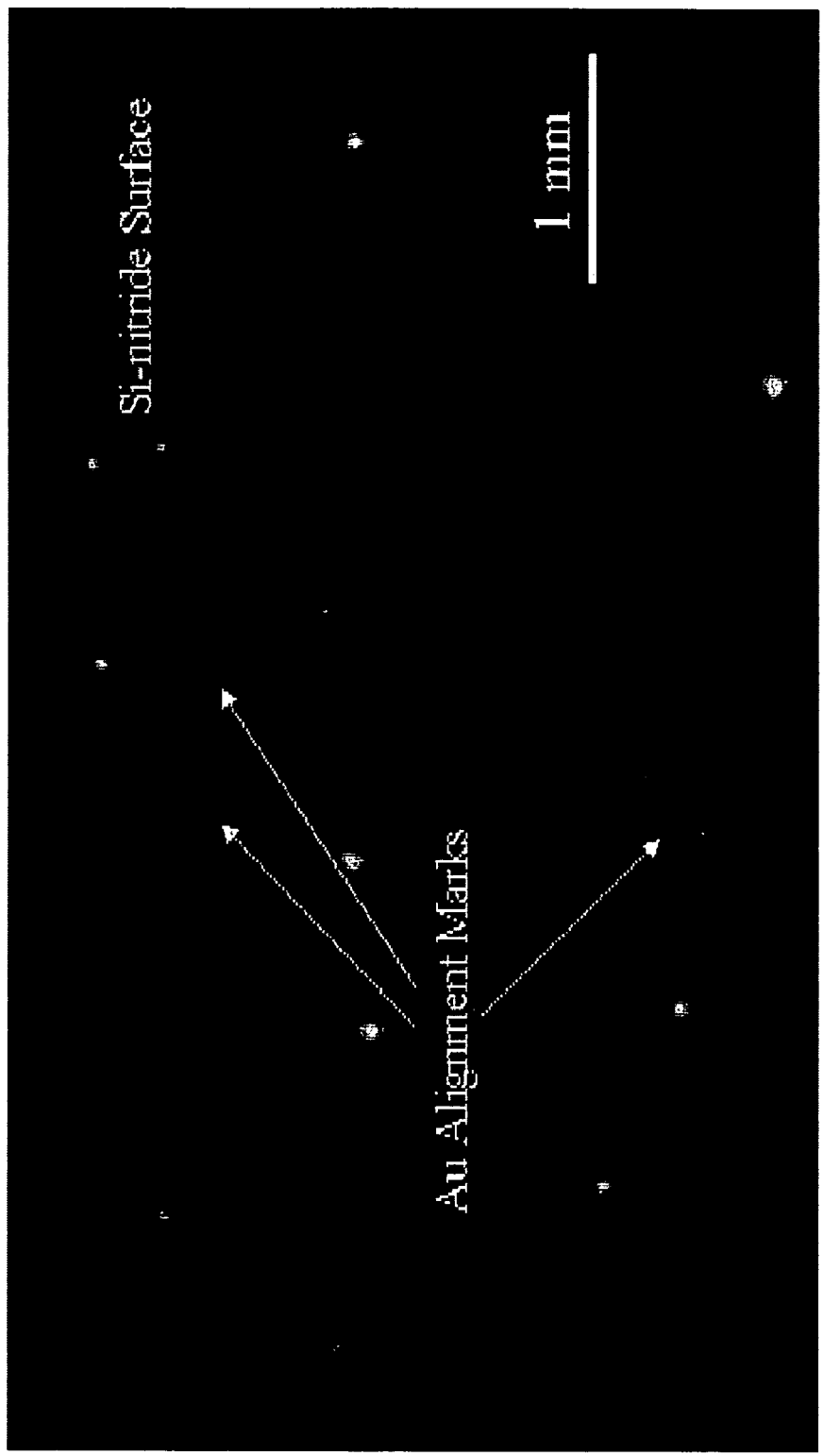
FIG. 10C is an image of a wafer with alignment marks on the silicon nitride membrane.

After deposition of the silicon nitride and metal layers, alignment marks 40 are made in the metal layer, as illustrated in FIGS. 10A-10B. A polymer that can be patterned via exposure to light, such as positive photoresist AZ1512, is used with standard photolithographic techniques to create photoresist islands in the shape of the desired alignment marks on the gold surface. These photoresist islands protect the underlying Au and Cr or TiW during the subsequent metal etch processes, resulting in alignment marks with the desired shape. Any pattern may be used that enables the features on the top and bottom of the wafer to be aligned. FIG. 10C shows one set of Au alignment marks created by this process on the silicon nitride layer.

Figure 11A:
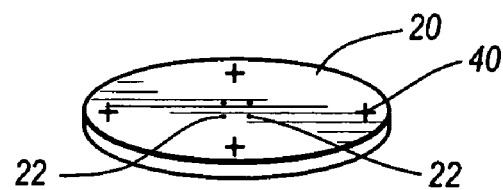
FIG. 11A is a perspective view of a wafer with nanoholes formed in the silicon nitride membrane.
Figure 11B:
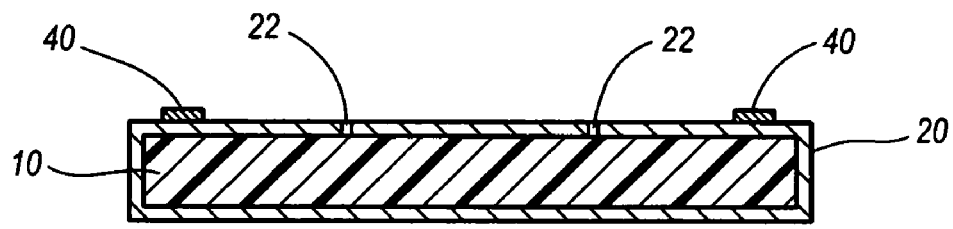
FIG. 11B is a cross-sectional view of a wafer with nanoholes formed in the silicon nitride membrane.
Figure 11C:
FIG. 11C is an image of a 5-by-5 array of 500 nm-diameter holes in a 0.75 μm poly(methylmethacrylate) layer.

Following metal deposition, nanoholes are created in membrane 20 by electron-beam followed by reactive ion etching (RIE), shown in FIGS. 11A-11B. Using electron beam lithography, an array of nanoholes are formed in a poly(methylmethacrylate) (PMMA) film 90 in registry with the alignment marks. FIG. 11C shows a scanning electron microscope image of an array of 500 nm-diameter holes in a 0.75 μm-thick PMMA film 90. The holes can be fabricated with a diameter ranging from tens of nanometers to tens of micrometers, depending on the application. Using the PMMA layer as the etch mask, the array of nanoholes is transferred into the silicon nitride membrane 20 by any suitable process. For example, the nanoholes may be created in the silicon nitride membrane also by photolithography followed by any dry plasma etching technique that is capable of selectively etching the silicon nitride. PMMA is then removed in an acetone bath.

Figure 11D:
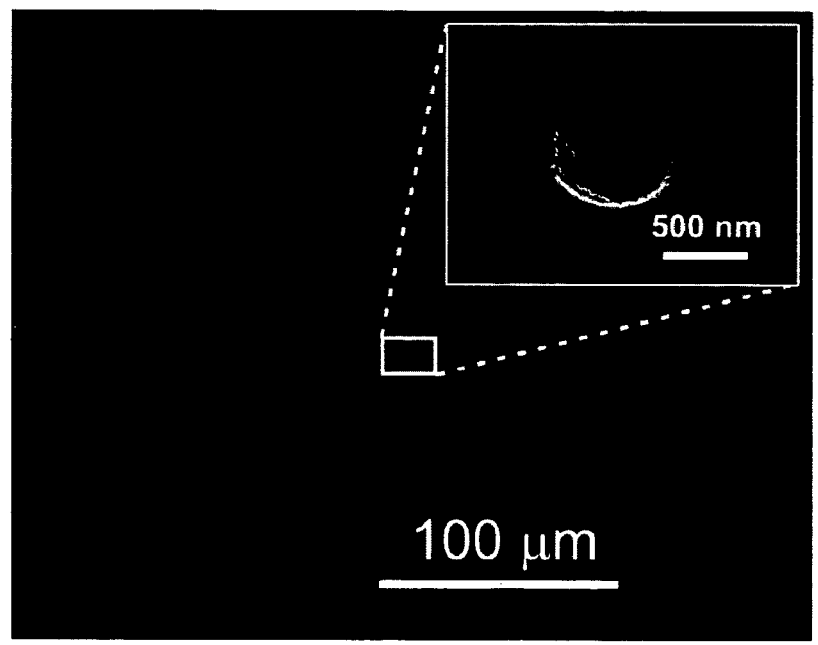
FIG. 11D is an SEM image of a 500 nm-diameter nanohole in a silicon nitride membrane.
Figure 11E:
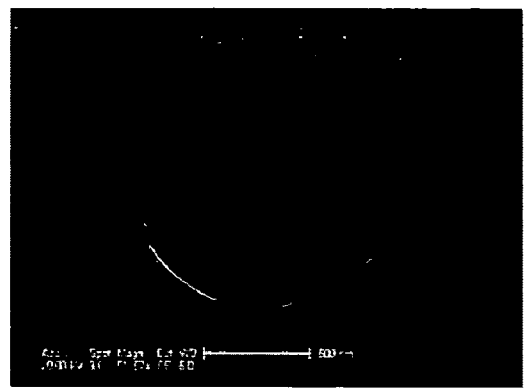
FIG. 11E is an SEM image of a 1000 nm-diameter nanohole in a silicon nitride membrane.
Figure 11F:
FIG. 11F is an SEM image of a 500 nm-diameter nanohole in a silicon nitride membrane.
Figure 11G:
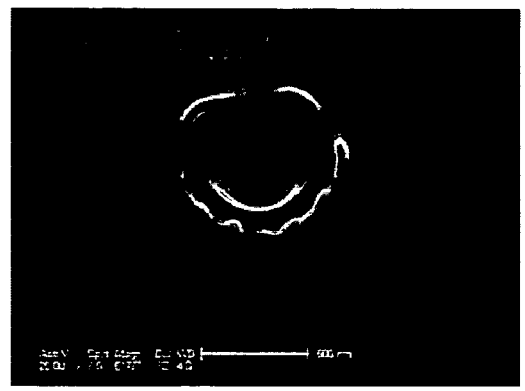
FIG. 11G is an SEM image of a less than 200 nm-diameter nanohole in a silicon nitride membrane.

Photolithography may be used to create nanoholes as small as about 500 nanometers. Smaller size nanoholes may be formed by electron beam lithography down to 50 nanometers. Nanohole sizes may be further shrunk by deposition of silicon nitride or silicon dioxide in the nanoholes. FIG. 11D is an SEM image of a 500 nm-diameter nanohole in a silicon nitride membrane. FIG. 11E is an SEM image of a 1000 nm-diameter nanohole in a silicon nitride membrane. FIG. 11F is another SEM image of a 500 nm-diameter nanohole in a silicon nitride membrane. FIG. 11G is an SEM image of a less than 200 nm-diameter nanohole in a silicon nitride membrane.

Figure 12A:
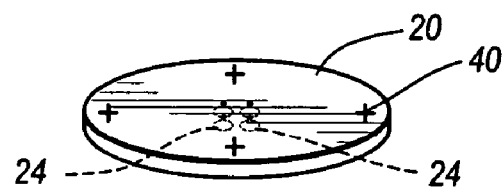
FIG. 12A is a perspective view of windows in the silicon nitride layer on the opposite side from the nanoholes.
Figure 12B:
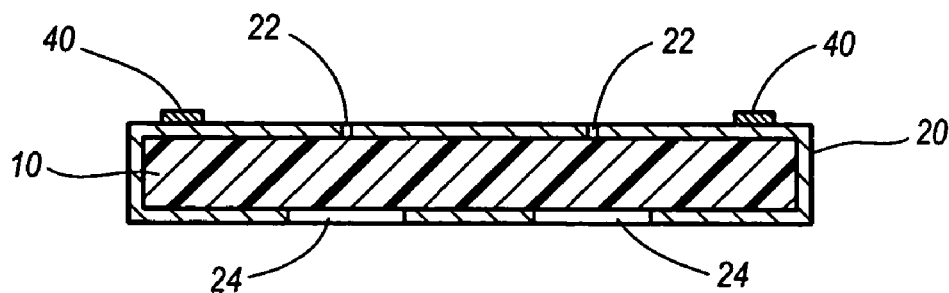
FIG. 12B is a cross-sectional view of windows in the silicon nitride layer on the opposite side from the nanoholes.
Figure 13A:
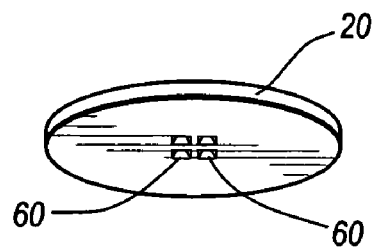
FIG. 13A is a perspective view of microwells etched into the wafer.
Figure 13B:
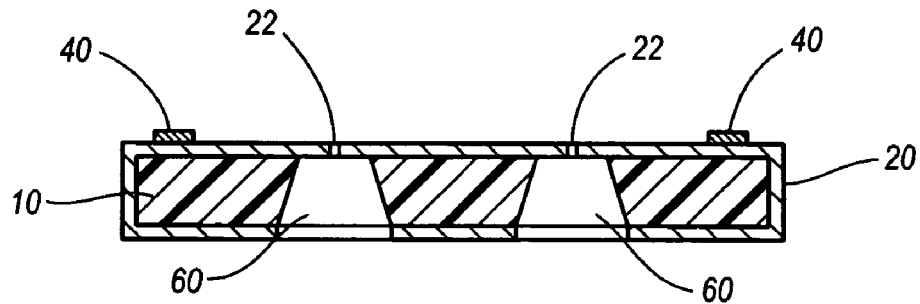
FIG. 13B is a cross-sectional view of microwells etched into the wafer.
Figure 13C:
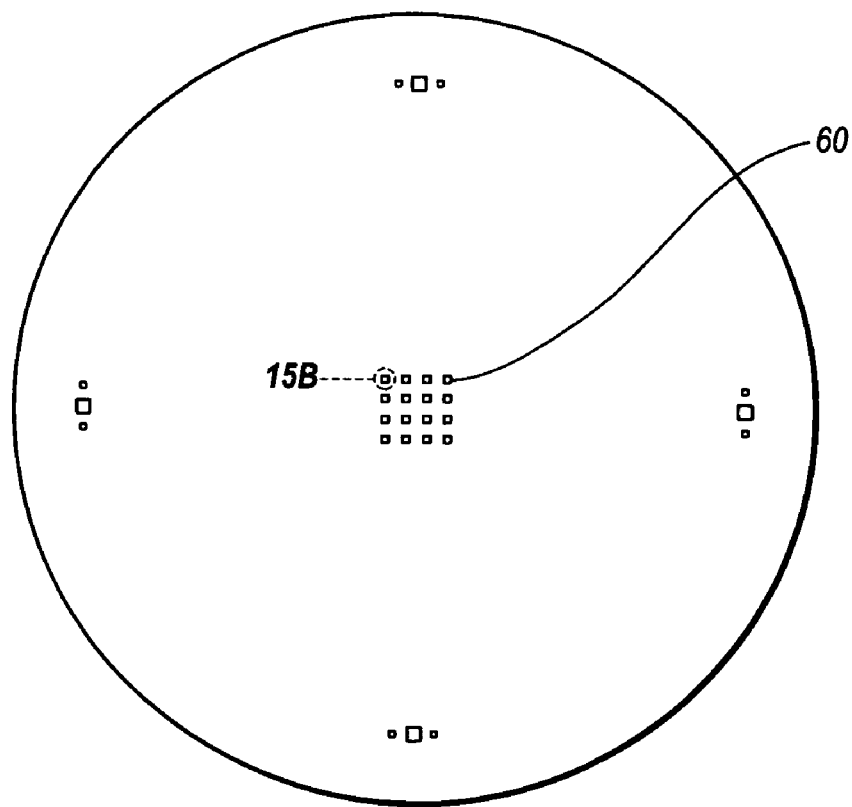
FIG. 13C is an top view of a 4-by-4 array of microwells etched into a 3-inch silicon wafer covered with a 300 nm silicon nitride layer.
Figure 13D:
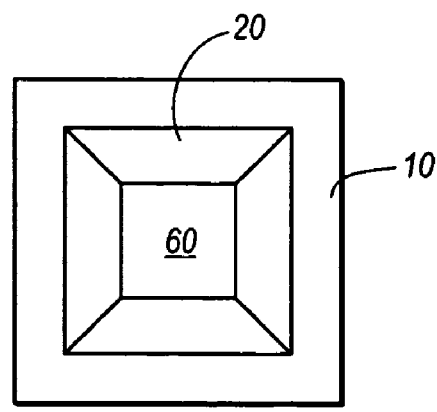
FIG. 13D is an enlarged view of a microwell.

FIGS. 12A-12B and FIGS. 13A-13B illustrate the next steps, etching of microwells windows 24 in silicon nitride layer 20 and anisotropic etching of microwells 60 in wafer 10. Square etch-windows 24 in the silicon nitride layer are formed on the backside of the wafer in registry with the alignment marks on the front side using standard photolithographic techniques and RIE, as shown in FIGS. 12A-12B. Only areas defined by window 24 will be etched away to create microwells. An aligner/exposer system with backside alignment capability is employed during the photolithography process. The wafer is anisotropically etched through the etch windows in a potassium hydroxide (KOH) bath (24.5% w/w, 80° C.) until the other side is reached, as shown in FIGS. 13A-13B. FIG. 13C is a top view of an array of microwells etched into a wafer with the inset magnifying one of these wells. This process suspends an array of silicon nitride membranes with a nanohole at the center of each. FIG. 13D is an image of a membrane taken from the back side (the microwell side) of the wafer.

Figure 14A:
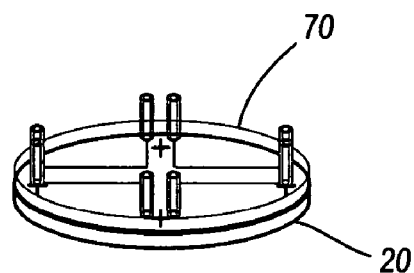
FIG. 14A is a top view of the device following the additional of a channel layer.
Figure 14B:
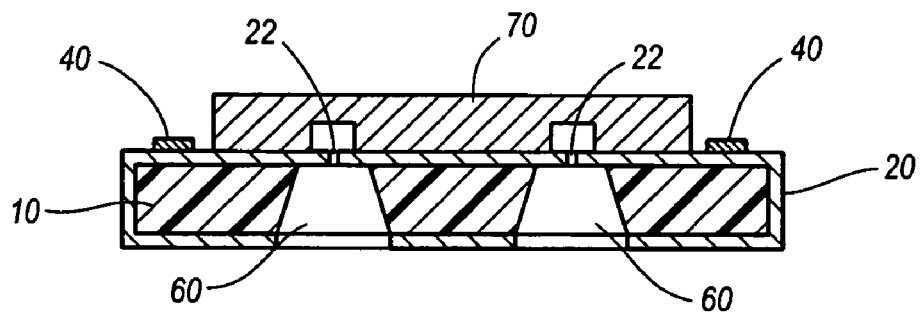
FIG. 14B is a cross-sectional view of the device following the addition of a channel layer.

FIG. 14A illustrates the step of microchannel assembly. A poly(dimethylsiloxane) (PDMS) channel layer 70 containing a network of microchannels 80 is assembled onto the front side of the wafer in registry with the suspended silicon nitride membranes. The microchannels are enclosed except for openings below the microwells at the suspended silicon nitride. Any polymer capable of sealing to the silicon nitride, such as polyimide, may be used instead of PDMS. PDMS layer 70 may be created separately and then sealed to the silicon wafer or may be applied directly. To get a good seal and adhesion between the silicon nitride and PDMS, both PDMS microchannels and wafer are treated in oxygen plasma to activate their surfaces. This allows a robust chemical bonding between them. Alternatively, a photocurable polymer may be directly patterned onto the silicon nitride layer by photolithography to form the channel layer. FIG. 14 illustrates the relative sizes of microchannel 80, nanohole 22 and bottom opening of microwell 62.

Modifications to the embodiments of the invention described above include the following:

Another wafer substrate such glass, quartz or sapphire can be used instead of silicon, and the fabrication process can be modified to accommodate this substrate of choice.

Silicon dioxide can be deposited onto the wafer and used as the membrane layer instead of silicon nitride. Other materials which are suitable for membrane materials include transparent polymers. These membrane materials can be deposited, grown or coated to form the appropriate membrane layer.

Another metal can be employed to create the alignment marks.

The number of membrane windows and microwells in the array can be increased or decreased depending on the needs of the application.

For creating the holes on the membrane, the electron beam lithography process can be substituted by a photolithographic process with a high-resolution chrome photomask. This will further lower the production costs of the device.

In place of PDMS, the microfluidic network can be fabricated from another suitable polymer.

Instead of assembling the microchannel network onto the wafer, the network can be created directly on the wafer surface by using a light-curable polymer photoresist (such as SU-8 from MicroChem Corp.) by standard photolithography.

The electrodes necessary for the electrophysiological applications of this device can be formed on the wafer surface by conventional photolithographic and metal-etch techniques. This will eliminate the need for external electrodes and increase the ease of use of the device, while decreasing the cost of operation.

EXAMPLES

Example 1

Figure 15A:
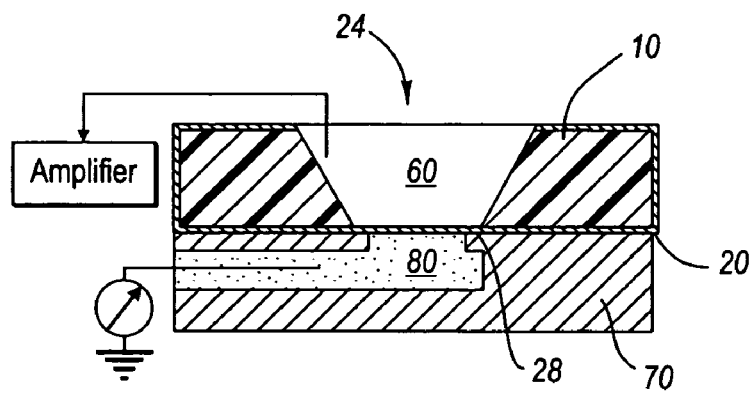
FIG. 15A is a cross-sectional view of a device without a nanohole in the silicon nitride membrane between the microwell and the micro-channel.
Figure 15B:
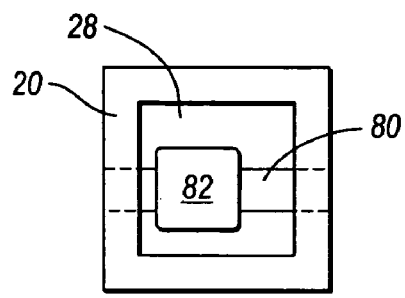
FIG. 15B is a top view of the device shown at FIG. 15A.
Figure 15C:
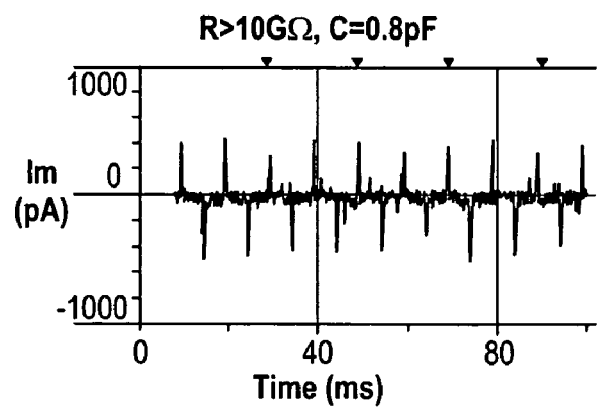
FIG. 15C shows electrical characterization results using the device shown in FIGS. 15A-15B.

FIG. 15A is a cross-sectional view of a device comprising a silicon wafer 10 defining a microwell 60. A PDMS layer 70 with a microchannel 80 is positioned with the microchannel aligned with a microwell 60. Membrane layer 20 does not have a nanohole below microwell 60. FIG. 15B is a top view of the device shown in FIG. 15A. Test experiments were conducted using this device to determine whether it provides results comparable to a traditional patch-clamp set-ups. The microwells and microchannels were filled with electrolyte fluid. A square-wave voltage pulse was applied between microwell and the microchannel. Electrical resistance and capacitance were measured. The results of the experiments are shown in FIG. 15C. In the absence of a nanohole the current did not flow, showing that the suspended silicon nitride layer provides a good insulation.

Example 2

Figure 16A:
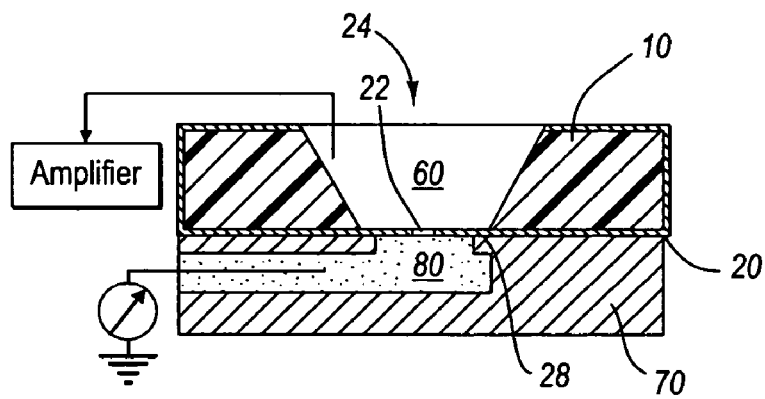
FIG. 16A is a cross-sectional view of a device with a nanohole in the nitride membrane and the microwell and the microchannel aligned.
Figure 16B:
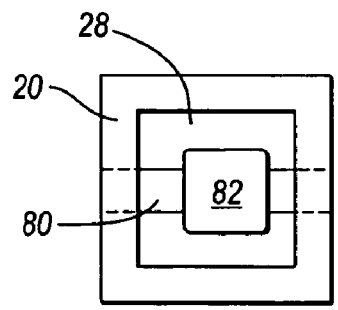
FIG. 16B is a top view of the device shown at FIG. 16A.
Figure 16C:
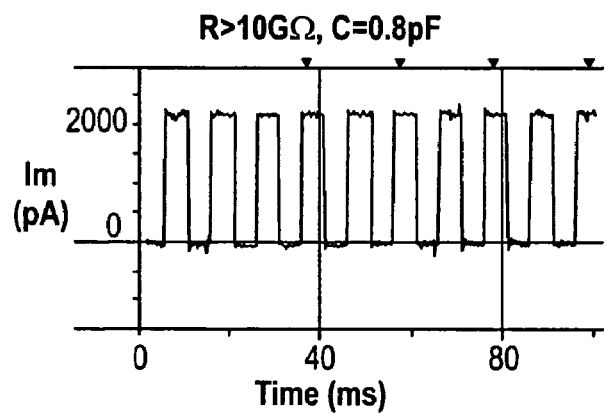
FIG. 16C shows electrical characterization results using the device shown in FIGS. 16A-16B.

FIG. 16A is a cross-sectional view of a device similar to the device described in connection with FIGS. 15A-15B except that membrane 20 defines a 1 µm nanohole 22 between microwell 60 and microchannel 80. FIG. 16B is a top view of the device shown in FIG. 16A. Electrical characterization of this setup was conducted in accordance with the protocol described above for Example 1. The results are shown at FIG. 16C. The resistance and capacitance values were comparable to micropipette resistance with a tip diameter of 1 µm.

Example 3

Figure 17A:
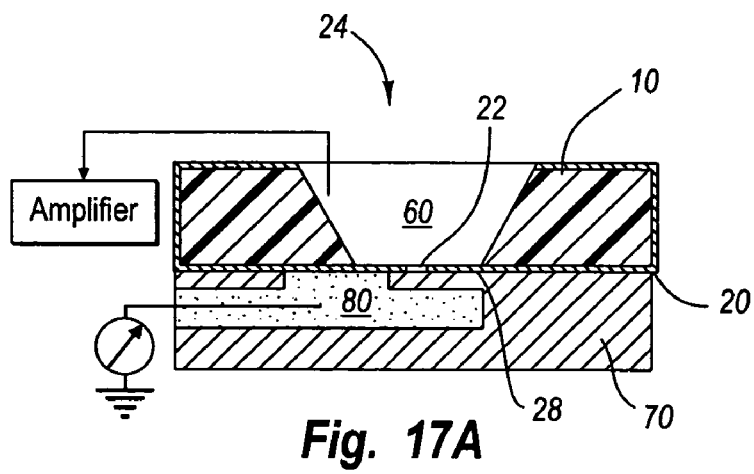
FIG. 17A is a cross-sectional view of a device with a nanohole in the silicon nitride membrane and the microwell and the microchannel misaligned.
Figure 17B:
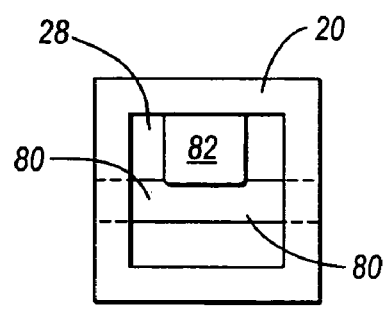
FIG. 17B is a top view of the device shown in FIG. 17A.
Figure 17C:
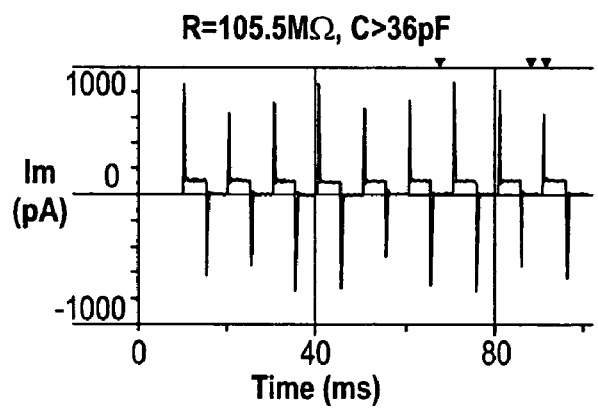
FIG. 17C shows electrical characterization results using the device shown in FIGS. 17A-17B.

FIG. 17A is a cross-sectional view of a device similar to the device described in connection with FIGS. 16A-B except that microchannel 80 is misaligned with microwell 60. FIG. 17B is a top view of the device shown in FIG. 17A. Electrical characterization of this setup was conducted in accordance with the protocol described above for Example 1. The results are shown at FIG. 17C. The results indicate that there was cross-talk or interference between the two electrodes of the amplifier through the silicon-backed (unsuspended) silicon nitride layer and the bulk silicon.

These examples illustrate that the device shown in FIGS. 16A-16B is optimized for patch-clamping applications.

It will be obvious to those having skill in the art that many changes may be made to the details of the above-described embodiments without departing from the underlying principles of the invention. The scope of the present invention should, therefore, be determined only by the following claims.

What is claimed is:

1. A device comprising:
   a substrate comprising a plurality of microwells, wherein at least one microwell is adapted to receive fluid, and wherein the microwell comprises a bottom opening;
   a membrane disposed on at least one surface of the substrate and suspended below the microwell bottom opening and wherein the suspended portion defines a nanohole; and
   a channel layer comprising a plurality of microchannels, wherein the channel layer is positioned such that the membrane is disposed between the substrate and the channel layer and such that a single microchannel is in fluid communication with the microwell via the nanohole,
   wherein the microwell and the single microchannel are fluidically isolated from a remainder of the plurality of microwells.

2. The device as claimed in claim 1, wherein the nanohole is sized to permit cells or biomolecules smaller than a designated size through the membrane while retaining larger cells or biomolecules behind the membrane.

3. The device as claimed in claim 1, wherein the nanohole has a diameter ranging in size from about 1 nanometer to about 50 microns.

4. The device as claimed in claim 1, wherein the membrane comprises silicon nitride.

5. The device as claimed in claim 1, wherein the membrane comprises silicon dioxide.

6. The device as claimed in claim 1, wherein the channel layer comprises a polymer.

7. The device as claimed in claim 1, wherein the channel layer comprises poly(dimethylsiloxane).

8. The device as claimed in claim 1, wherein the nanohole is sized to permit a single strand of DNA or protein to pass through the nanohole.

9. The device as claimed in claim 1, wherein the nanohole measures between about 1 to about 3 nanometers in diameter.

10. A method for providing access to a cell or biomolecule comprising:
    obtaining a device for containing a cell or biomolecule, wherein the device comprises a plurality of microwells that each comprise a bottom opening, and a membrane positioned below the bottom openings of the plurality of microwells with a separate portion suspended across each bottom opening, wherein each of said suspended portions of the membrane defines a nanohole positioned below the bottom opening of one of the microwells, and wherein each of the plurality of microwells is fluidically isolated from the rest of the plurality of microwells and each of said suspended portions of the membrane is fluidically isolated from the rest of the suspended portions of the membrane; and
    positioning the cell or biomolecule on one side of one of the suspended portions of the membrane, such that the cell or biomolecule can be accessed via the nanohole that is defined by said one of the suspended portions of the membrane.

11. The method of claim 10, wherein the device further comprises a microchannel layer, wherein the microchannel layer defines at least one microchannel with an opening under the nanohole.

12. The method of claim 11, wherein the microchannel provides access to the cell or biomolecule.

13. The method of claim 10, further comprising applying suction to the side of the suspended portion of the membrane opposite the cell or biomolecule to position the cell or biomolecule at the nanohole.

14. The method of claim 10, wherein the device is adapted to enable the cell or biomolecule to be automatically guided to the nanohole when suction is applied to the other side of the nanohole to position cell or biomolecule.

15. The method of claim 10, wherein the positioning step is achieved via the microwell.

16. The method of claim 11, wherein the positioning step is achieved via the microchannel.

17. A device comprising:
    a substrate defining multiple microwells that are fluidically isolated from each other, wherein each of the microwells defines a bottom opening;
    a membrane layer positioned on at least one surface of the substrate and below the bottom opening of at least one of the microwells and defining at least one nanohole, wherein a nanohole is positioned below the bottom opening of a single microwell; and
    a polymeric insulator positioned below the membrane layer, wherein the polymeric insulator defines a microchannel positioned below the nanohole in the membrane layer, wherein the membrane layer is at least partially suspended above the microchannel defined by the polymeric insulator,
    wherein the membrane layer, the microchannel and the bottom opening of the single microwell are configured such that a fluid contained in the microchannel contacts the membrane layer only at a portion of the membrane which is below the bottom opening of the single microwell.

18. The device as claimed in claim 17, wherein the configuration of the membrane layer, the microchannel and the bottom opening of the single microwell prevents fluid contained in the microchannel from contacting a portion of the membrane layer which is below the substrate.

19. The device as claimed in claim 17, wherein the microchannel has a portion with an area below the bottom opening of the single microwell, which is smaller than the area defined by the perimeter of the bottom opening of the single microwell.

20. A method of manufacturing a device for providing access to cells or biomolecules comprising:
    obtaining a substrate with a top side and a bottom side;
    forming a membrane layer on the substrate;
    forming a plurality of windows in the membrane layer on the top side of the substrate and etching a plurality of microwells in the substrate at the window, wherein the microwells are fluidically isolated from each other;
    forming nanoholes in the membrane layer, wherein the nanoholes are positioned on the bottom side of the substrate such that a separate nanohole is positioned under each of the microwells; and
    providing channel multiple channels in a channel layer attached to the bottom side of the substrate, wherein each channel is enclosed within the channel layer except for at an opening positioned under the a single nanohole.

21. A method of manufacturing a device for providing access to cells or biomolecules comprising:
    obtaining a silicon substrate with a top side and a bottom side;
    forming a silicon nitride layer on the substrate;
    depositing a metal layer above the silicon nitride layer and creating photoresist islands using a photoresist polymer;

etching a plurality of nanoholes in the silicon nitride layer by reactive ion etching, using a film containing a nanohole as an etch mask;

lithographically etching a plurality of microwell windows in the silicon nitride layer, wherein the microwell windows are positioned opposite the plurality of nanoholes, using the photoresist islands as a guide;

anisotropically etching a microwell at each microwell window such that each microwell is fluidically isolated from the rest of the microwells;

obtaining a channel layer comprising a plurality of channels, with each channel being enclosed within the channel layer except at a single channel opening; and sealing the channel layer to the silicon nitride such that each channel opening is positioned beneath a separate nanohole.

\* \* \* \* \*